United States Patent
Shelvey

(10) Patent No.: US 6,756,467 B2
(45) Date of Patent: *Jun. 29, 2004

(54) CURABLE COMPOSITIONS

(75) Inventor: Michael Francis Shelvey, York (GB)

(73) Assignee: BSN Medical, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/092,187

(22) Filed: Mar. 5, 2002

(65) Prior Publication Data

US 2002/0128421 A1 Sep. 12, 2002

Related U.S. Application Data

(63) Continuation of application No. 09/029,971, filed on May 26, 1998, now Pat. No. 6,353,077, which is a continuation of application No. PCT/GB96/02258, filed on Sep. 13, 1996.

(30) Foreign Application Priority Data

Sep. 13, 1995 (GB) .............................................. 9518749

(51) Int. Cl.⁷ .............................................. C08G 18/10
(52) U.S. Cl. ...................... 528/58; 528/59; 252/182.22; 602/8
(58) Field of Search ..................... 528/58, 59; 252/182, 252/22; 602/8

(56) References Cited

U.S. PATENT DOCUMENTS 4,427,003 A * 1/1984 Fennimore et al.
4,705,840 A * 11/1987 Buckanin et al.
4,824,595 A * 4/1989 Richter et al.
5,027,804 A * 7/1991 Forsyth et al.

FOREIGN PATENT DOCUMENTS

| GB | 1578895 | * 11/1980 |
| WO | 81-00671 | * 3/1981 |
| WO | 88-02636 | * 4/1988 |
| WO | 94-02525 | * 2/1994 |
| WO | 96-06873 | * 3/1996 |

* cited by examiner

Primary Examiner—Rachel Gorr
(74) Attorney, Agent, or Firm—Adams Evans P.A.

(57) ABSTRACT

A resin system including a water curable isocyanate functionalized prepolymer, a first catalyst chemically bound-in to the prepolymer, and a second catalyst soluble in water and insoluble in the prepolymer.

4 Claims, No Drawings

CURABLE COMPOSITIONS

This application is a continuation of 09/029,971, filed May 26, 1998, now issued as U.S. Pat. No. 6,353,077, which is a continuation of PCT/GB96/02258, filed Sep. 13, 1996.

TECHNICAL FIELD AND BACKGROUND OF THE INVENTION

The present invention relates to curable resin compositions and in particular to isocyanate based resin systems suitable for use in medical applications, such as orthopaedic casting and splinting.

A favored method for curing isocyanate resins is to use water curing. Water curing can be achieved by many means, for example the resin being immersed in water, contact with atmospheric moisture or by being sprayed with water after application.

As used herein, "water curable" means that the resin system is capable of hardening to a rigid or semi-rigid structure on exposure to water.

Any isocyanate based resin system depending on the reaction of an isocyanate with water, amine or alcohol group for curing may benefit from the use of catalysts to speed up the curing so that the resin sets in an acceptably short time.

The use of inorganic carbonate catalysts has been proposed with isocyanate resin systems, however the shelf life was affected in the presence of any moisture, as the catalyst is in direct contact with the resin and was set off in the presence of moisture. More recently different catalysts based on tertiary amines have been used with isocyanate functionalized resin systems.

The use of inorganic carbonate catalysts has been proposed with functionalized isocyanate resin systems in Patent Application WO 88/02636, U.S. Pat. Nos. 5,027,804 and 4,427,003; however the shelf life may be affected in the presence of any moisture, as the catalyst is in direct contact with the resin and would be set off in the presence of moisture. More recently, alternative catalysts based on tertiary amines have been used with isocyanate functionalized resin systems.

Reactive tertiary amines are rarely fully chemically incorporated into the polyurethane during the isocyanate-water reaction. In addition, such tertiary amines may be vaporised by the exotherm generated during the polyurethane reaction. Thus, there is the possibility that catalyst may leach or evaporate from the resin system during cure or after curing. Such amines may have a strong odor and the potential inhalation and absorption toxicity of tertiary amines is well known.

Patent Application WO 94/02525 partially addresses the problems encountered with tertiary amine catalysts by modifying reactive tertiary amine catalysts by mixing under reaction conditions a reactive tertiary amine, a polyol and an organic isocyanate compound to give a catalyst which has a higher molecular weight and may therefor be retained more.

Patent Application WO 94/05475 discloses a tertiary amine as a polyurethane reaction catalyst, where the catalyst is added to a binder containing isocyanate groups. Lignocellulose fibres are coated with the binder and then shaped into a mat which is pressed under the influence of heat to form a board, where the catalyst is subsequently built into the board.

However such catalysts may still be prone to leaching especially when used in a water curable isocyanate composition.

It may be possible to use a lower level of catalysts to reduce the problems discussed above, however such a catalyst is unlikely to be suitable for rapid cure systems, as would be required for a splinting material.

The present invention seeks to overcome these disadvantages by providing a curable resin composition with catalysts which are not a potential hazard due to leachable components.

The use of a chemically bound-in tertiary amine catalyst would overcome the problems associated with the leaching of catalyst. "Chemically bound-in" means the catalyst is ionically and/or covalently bound to the curable isocyanate functionalized prepolymer.

Furthermore the use of more than one catalyst may benefit the curing speed of isocyanate functionalized resin systems.

Surprisingly it was found that the curing reaction of a water curable isocyanate functionalized resin, when catalyzed by a first and a second catalyst resulted in a greatly increased curing rate of the resin as the two catalysts together showed a synergistic effect.

The synergistic effect described in this invention is the increase in the reaction rate between water and isocyanate functionalized prepolymers in polyurethane/urea synthesis.

Thus according to the present invention there is provided a resin system comprising at least a water curable, isocyanate functionalized prepolymer and a first and second catalyst component wherein the first catalyst is chemically bound-in to the prepolymer and the second catalyst is not chemically bound-in.

Chemically bound-in catalysts include catalysts bonded covalently and/or ionically to the isocyanate functionalized prepolymer.

Preferably the first chemically bound-in catalyst is covalently bound-in to the prepolymer.

Preferably the first catalyst is a tertiary amine catalyst.

Suitable tertiary amine catalysts comprise both a tertiary amine group and an isocyanate reactive group.

The term "isocyanate reactive group" refers to a group which forms a covalent bond when reacted with an isocyanate group (—NCO) under appropriate conditions, these include for example hydroxy and amine groups as well as carboxylic acids, thiols, anhydrides, urethanes, ureas and other such groups with an active hydrogen atom known to one skilled in the art.

Preferably the chemically bound-in tertiary amine catalyst is covalently bound-in to the prepolymer.

The bound-in tertiary amine group may be present at any appropriate location in the isocyanate prepolymer. For example they may be introduced at an end of the isocyanate prepolymer molecules via a capping reaction, they may be present on a side chain extending from the main polymer backbone, or may be part of the polymer backbone itself. The tertiary amine group may be optionally substituted with substituents which do not substantially adversely affect the reaction of the tertiary amine group with isocyanate groups or the catalytic effect of the tertiary amine groups when present in the isocyanate prepolymers of the resin composition of the present invention.

Appropriate molecules for reacting with the polyisocyanates so as to form the prepolymers of the composition of the present invention may include but are not limited to the following molecules:

1-(2-Hydroxyethyl) pyrrolidine, 1-methyl piperazine,
1-methyl-2-piperidine methanol, 1,4-6is(2-hydroxyethyl) piperazine
2[2-(dimethylamino) ethyl]methyl amino ethanol, gramine, 3-morpholino-1,2-propanediol,
1,4-bis(3-aminopropyl)piperazine, tropine,
3-aminopropyl morpholine, 4,2-hydroxyethyl morpholine,
3,3-diamino-N-methyl dipropylamine,
1,4-bis(2-hydroxypropyl)-2-piperazine,
1-(2-hydroxypropyl) imidazole, 3-dimethyl amino propanol and β-hydroxy-4-morpholine propane sulphonic acid.

The chemically bound-in tertiary amine catalyst may be a single species or mixture of species. Further, several species of such bound-in tertiary amines may be present within a prepolymer composition or within one isocyanate functionalized prepolymer molecule.

Any one of the prepolymer molecules may contain a single bound-in tertiary amine catalyst of a single species or more than one tertiary amine catalyst of a number of species.

In addition any one prepolymer molecule may include more than one tertiary amine catalyst either present on a side chain, as end groups or part of the polymer backbone, for example, when the tertiary amine catalysts include two or more isocyanate reactive catalysts and act as chain extenders.

The isocyanates used to react with the tertiary amine catalyst comprising both a tertiary amine group and an isocyanate reactive group may be any suitable isocyanates well known in the art, for example aliphatic, cycloaliphatic, aromatic or heterocyclic isocyanates. Preferably aliphatic isocyanates are used.

Whatever species of tertiary amine containing molecules are utilized to prepare a bound-in catalyst, it is preferred that they comprise less than 10% by weight more preferably from 0.1 to 5% by weight of the curable composition.

The second catalyst is preferably 0.05 to 10% and more preferably 0.1 to 5% by weight of the curable composition. The second catalyst is preferably water soluble but insoluble in the prepolymer. The second catalyst is preferably a solid inorganic catalyst. For example, the second catalyst is aptly a group I metal salt, such as a group IA metal salt, such as a group IA metal carbonate. An apt example of a group IA metal carbonate is potassium carbonate.

Suitably the first and second catalyst together comprise less than 7.5% by weight of the resin system.

Preferably equal amounts of the first and second catalysts are added to the resin system, for example 1.0%, 1.25%, 2% or 2.5% of each of the first and second catalyst by weight of the resin system may be added.

The second catalyst is dispersed in the curable composition of the invention using methods known to those skilled in the art.

A problem often associated with the use of inorganic carbonate catalysts is where the shelf life of the curable resin system is reduced due to the increased reactivity of the isocyanate functionalized prepolymer with atmospheric moisture in the presence of a carbonate catalyst. This may be avoided by coating the carbonate catalyst with a coating that is insoluble in atmospheric moisture and is soluble in water, or water pervious once the coating is hydrated.

A preferred feature of the present invention, although not essential is the pre-treatment of the selected solid inorganic catalyst with a hydrophilic coating, before dispersion in the prepolymer. This reduces the risk of aging of the resin system.

The hydrophilic coating may be any suitable coating that will dissolve on contact with water or become hydrated with water such that the hydrated coating becomes water pervious, for example, polyvinyl alcohol (PVA) or polyhydroxyethylmethacrylate (poly HEMA).

Further according to the present invention there is provided a process for making a curable resin system as hereinbefore described wherein isocyanates and molecules comprising both a tertiary amine group and an isocyanate reactive group are reacted to give any isocyanate functionalized prepolymer into which is mixed a coated solid inorganic catalyst.

For a reaction based on an aromatic isocyanate functionalized resin the use of two catalysts as hereinbefore described would allow an overall reduction in the amount of catalyst required, therefore reducing toxilological aspects and costs.

This invention is particularly suitable for the curing reaction of aliphatic isocyanate functionalized prepolymers which are well known in the art for having a much slower cure time than aromatic isocyanate functionalized prepolymers, and have therefore been considered unsuitable up until now for use in orthopaedic splinting applications.

The use of aliphatic isocyanates allows the preparation of prepolymers with a larger range of viscosities. The use of aromatic isocyanates usually results in more viscous prepolymers which may not be as suitable for orthopaedic applications. Furthermore, polymers base on aliphatic isocyanates do not tend to yellow on aging.

The use of at least two catalysts as hereinbefore described comprising in total preferably less than 10% by weight of the curable composition has made it possible to consider the use of aliphatic based isocyanates for orthopaedic splinting materials.

In a further embodiment of the present invention there is provided an orthopaedic splinting material comprising a flexible substrate carrying a resin system as hereinbefore described.

Preferred formulations according to the present invention can include effective amounts of a variety of additives conventional in the art. These additives may comprise fillers, pigments, fragrances, surfactants lubricants, or mixtures thereof. Effective amounts and amounts sufficient to provide the benefits of the additive.

Suitably powdered fillers include but are not limited to talc, calcium carbonate, fumed silica sold under the trade name CAB-O-SIL, alumina and fibrous reinforcing fillers such as wollastonites (calcium metasilicate), to impart desirable viscosity and handling characteristics.

The fillers may be present as single chemical species or as mixtures and, when used, are aptly present in an amount of up to 50% w/w, preferably up to 20% w/w and aptly at least 1.0% w/w of the resin.

Although the splinting material of the present invention is described in terms of an "orthopaedic splinting material", the term is also intended to embrace casts, supports and braces, where such casts, splints, supports and braces do not necessarily surround the whole limb or other body portion.

The resin system used in the bandages of the invention according to the invention may be carried on any substrate suitable for a casting, splinting, bracing or support material.

The resin system employed in the invention may be coated, laminated, sprayed or impregnated onto a suitable substrate using conventional methods in the art. Aptly the splinting material of the invention is prepared by nip-coating the resin system onto the substrate.

Aptly the splinting material of the present invention may be prepared by using a substrate carrying the second catalyst and subsequently coating or impregnating the substrate with a prepolymer as hereinbefore described comprising an isocyanate functionalized prepolymer and the first catalyst which is chemically bound-in to the prepolymer.

For use as an orthopaedic splinting material, the viscosity of the resin system is preferably suitable for application to a substrate. Furthermore the viscosity is preferably such that the resin system remains in place on and within the substrate, while in storage and during curing.

Aptly the resin systems of the invention have viscosities ranging from 1,000 to 100,000 $mPas^{-1}$, and more preferably from 40,000 to 60,000 $mPas^{-1}$.

A preferred substrate is a flexible fabric carrier which may be a woven, knitted or non woven fabric which can carry enough of the resin system of the invention to ensure that the resultant splint has adequate strength. The substrate should be sufficiently porous to allow water to come into contact with the carried resin system when the splinting material is immersed in water. The substrate may be in the form of tapes, bandages, sheets or other conventional forms, apt for preparing for example orthopaedic casting bandages, splinting materials, braces or supports.

Suitable materials for forming the substrate include polyester, nylon, polypropylene, polyamides, polyolefins and glass fibre or mixtures thereof. Examples of such substrates are disclosed in U.S. Pat. Nos. 4,427,002, 4,627, 424 and EP 326,285.

Aptly the substrate may be a mesh having openings through it to enable the water to penetrate into the rolled bandage to contact all parts of the resin system. The openings will permit circulation of air and aid evaporation of moisture from the skin beneath the cured cast.

Preferably the mesh is of a loose weave or knit so as to allow at least partial impregnation as well as coating by the resin system.

The amount of resin carried by the substrate may vary depending on the intrinsic properties of the resin system and should be sufficient to ensure that the resultant cast has adequate strength.

Suitable amounts range from 30 to 80% w/w of the resin system which are calculated using the equation:

$$\frac{\text{weight of (substrate + resin)} - \text{weight of (substrate)}}{\text{weight of (substrate + resin)}} \times 100\%$$

Preferably 40 to 70% w/w and most preferably 50 to 65% w/w of the resin system are used.

The orthopaedic splinting materials may be used to form a hardened cast by wetting and shaping the wet material around a body member or part thereof and allowing the resin system to cure.

Upon curing the resin system generally becomes bonded, physically or chemically to the substrate.

Aptly wetting is achieved by immersing the splinting material in water, and removing any excess water, for example, by squeezing the splinting material several times before application to the body member.

When removed from the water the splinting material can be readily wrapped about the limb which is to be immobilized and wherein the limb is preferably protected with a conventional underlying stockinet or padding.

Extra cushioning may be provided in the form of undercast padding.

An alternative method for forming a cast or splint comprises applying the splinting material of the invention to the body member to be immobilized followed by spraying the material with water.

The curing reaction of the resin system should be sufficiently slow to allow the splinting material of the invention to be positioned and shaped before the material becomes unworkable. Suitable working times are aptly 1 to 6 minutes more aptly 2 minutes to 4 minutes. The curing reaction of the resin system should, however, be sufficiently fast to permit the formed cast or splint to become supportive and load-bearing as soon as possible after completion of working. Aptly the material will set and become supportive between 5 and 30 minutes, more aptly within 15 minutes and particularly in the case of a splint, will aptly become load-bearing within 60 minutes, more aptly after 10 minutes.

The splint may be readily removed by conventional means such as by cutting with a convention vibrating sawtooth disc.

The orthopaedic splinting material of the invention should be protected during storage from water and moisture vapor to prevent a premature setting taking place. The splinting material can be conventionally packaged in heat sealed pouches such as metal foil polyethylene laminate pouches.

The present invention will now be described without limitation thereof with reference to the accompanying examples. It should be understood that normal precautions for excluding moisture during the chemical reactions were employed.

PolyHEMA Coated Potassium Carbonate

Preparation of polyHEMA coated potassium carbonate was carried out by charging a resin flask with 2-hydroxyethylmethacrylate (250 g), potassium carbonate (250 g, 90±m sieved and milled) and dry ethyl acetate (2.5L). The flask was provided with a stirrer, purged with nitrogen, and stirred for three hours, followed by addition of bis (4-t-butyl cyclohexyl) peroxydicarbonate (BCHPC, 2% by weight) and stirring for 5 hours at 55° C.

At the end of the reaction bulking was evident. The material was collected by vacuum filtration and washed with ethyl acetate. The material was then dried for two days in a vacuum oven.

The percentage yield was 96%.

PREPARATION OF ALIPHATIC ISOCYANATE FUNCTIONALIZED RESINS

The materials and amounts used in Examples 1 to 5 are shown in Table 1 below.

TABLE 1

| Materials (g) | Example 1 | Example 2 | Example 3 | Example 4 | Example 5 |
|---|---|---|---|---|---|
| PEG 3350 | 1.42 | 5.67 | 5.64 | 2.80 | 0.9 |
| PEG 1500 | 3.82 | 15.22 | 15.15 | 7.52 | 5.37 |
| PEG-5E0 | 1.84 | 7.31 | 7.27 | 3.61 | — |
| Methy-N | 2 | 2.50 | 4.98 | 5.01 | 3.75 |
| Piperazine | 2.17 | 6.51 | 4.39 | — | |
| Piperidine | 5.02 | 19.98 | 19.88 | | 3.25 |
| EP2001 | 11.49 | 45.92 | 45.88 | | 11.80 |
| DN3400 | 24.24 | | | | 24.19 |
| | | 96.90 | 96.82 | 9.87 | |
| HDT-LV | 0.1 | 0.04 | | 22.89 | 0.1 |
| Metatin 812ES | | | 0.4 | 48.30 | 0.2 |
| % of bound-in catalyst w/w | 0.0% | 1.25% | 2.5% | 5.0% | 7.5% |

The following procedure illustrates the preparation of water curable resin compositions as formulated in Examples 1 to 5 in Table 1.

METHOD FOR PREPARING RESINS
EXAMPLES 1 to 5

The polyols (PEG 3350, PEG 1500, BPA SEQ EP 2001) were weighed into a predried flask, heated to 60° C. and stirred to give a homogeneous mixture. Approximately 70% of this mixture was decanted into a predried flask, provided with a stirrer, an inlet port and flushed with nitrogen. To this was added the first isocyanate (DN3400) and the metatin before stirring for one hour at 90° C. Subsequently the second isocyanate Tolonate HDT-LV was added under nitrogen while stirring.

The tertiary amine (methyl-N-piperazine) was diluted by mixing with the remaining 30% of the polyol and then added to the isocyanate mixture. Stirring continued for a further hour at 90° C., before cooling the mixture.

PREPARATION OF RESIN SYSTEMS PREPARED IN EXAMPLES 1–4 CONTAINING POTASSIUM CARBONATE

PolyHEMA coated potassium carbonate was prepared as herein before described to give a solid catalyst comprising 50% potassium carbonate and 50% polyHEMA.

Coated potassium carbonate (2.5%, 5% and 7.5% w/w) was stirred into the resins prepared in Examples 1–4 and the curable compositions were sealed in an airtight container.

Preparation of Orthopaedic Splinting Materials

The resin formulations obtained in Examples 1 to 5, with and without coated potassium carbonate were coated onto dry glass fibre substrates by passing the substrate through the resin system followed by passing the coated substrate through a nip roller, adjusted to a suitable pressure for obtaining a coating weight of 50–60% w/w coating. The coated substrate was then dipped in water, squeezed several times to allow water to impregnate throughout the substrate, and used to bandage around the forearm of an artificial limb (which approximated the contours of a human forearm).

It was found that a hard, smooth cast was formed within 4–100 minutes (Table 2) when the wet, impregnated substrate was applied. The resin has a viscosity which allowed the splinting material to be easily worked so that a smooth cast could be formed. The effect on cure time of adding a bound-in catalyst and a solid inorganic catalyst in various amounts is illustrated in Table 2 and summarized in Table 3 below.

TABLE 2

Average Curing Time (minutes)

| Bound-in tertiary amine catalyst % w/w | POTASSIUM CARBONATE* % w/w | | |
|---|---|---|---|
| | 1.25% | 2.5% | 3.75%* |
| Example 1 0% | 60+ | — | 13.5 | 12.0 |
| Example 2 1.25% | 26 | 7 | — | |
| Example 3 2.5% | 12.5 | — | 4.5 | |
| Example 4 5.0% - | 11.3 | — | 5.0 | |
| Example 5 7.5% | 7.5 | — | — | |

TABLE 2-continued

Average Curing Time (minutes)

| Bound-in tertiary amine catalyst % w/w | POTASSIUM CARBONATE* % w/w | | |
|---|---|---|---|
| | 1.25% | 2.5% | 3.75%* |

*Potassium carbonate (K2C03) was added as K2CO coated with Poly-HEMA (1:1). [PolyHEMA added without K2C03 had no effect on the reaction rates.]
*It was practically not feasible to add more than 3.75% w/w 4003 (7.5% w/w coated K$_2$CO$_3$).

TABLE 3

| Total catalyst level | Catalyst | Cure time (mins) |
|---|---|---|
| 2.5% w/w | 2.5% bound-in tertiary amine catalyst | 12.5 |
| | 2.5% K$_2$C0$_3$ | 13.5 |
| | 1.25% K$_2$C0$_3$ and 1.25% bound-in amine catalyst | 7 |
| 5.0% w/w | 5.0% bound-in tertiary amine catalyst | 11.3 |
| | 2.5% K$_2$C0$_3$ and 2.5% bound-in tertiary amine catalyst | 4.5 |
| 7.5% w/w | 7.5% bound-in tertiary amine catalyst | 7.5 |
| | 2.5% K$_2$C0$_3$ and 5.0% bound-in tertiary amine catalyst | 5.0 |

TABLE 4

Materials Used in Examples 1–5

| Description/Supplier | Components |
|---|---|
| PEG 3350 | Polyethylene Glycol (Mwt 335C) |
| BPA SEQ | Ethoxylated Bis-phenol A |
| Jeffamine TM EDR-148 (obtainable from Huntsman Corp.) | Diamine Chain Extender |
| Methyl-n-piperazine (obtainable from Aldrich Chemical Co UK Ltd) | Bound-in Catalyst |
| Desmodur N3400 (obtainable from Whitfield Chemicals) | Aliphatic Isocyanate HDI based (hexamethylene diisocyanate) |
| Anitfoam MSA (obtainable from Ellis-Everard Inc USA) | Silicone based Antifoaming agent |
| Metatin 813E5 | Tin Catalyst |
| Coated K$_2$CO$_3$ | 50/50 PolyHEMA Coated Potassium Carbonate |
| PEG 1500 | Polyethylene Glycol (Mwt 1500) |
| Voranol TM EP2001 (obtainable from K&K Greeff Ltd. UK) | Ethyleneoxide end-capped Polypropylene Glycol |
| Tolonate TM HDT-LV (obtainable from Rhone Poulenc | Aliphatic Isocyanate (HDI Trimer) |

I claim:

1. A resin system, comprising:
   (a) a water curable isocyanate functionalized prepolymer;
   (b) a first catalyst chemically bound-in to said prepolymer, wherein said first catalyst comprises a mixture of ionically and covalently bound-in catalysts; and
   (c) a second catalyst soluble in water and insoluble in the prepolymer, wherein said second catalyst includes a hydrophilic coating.

2. A method for treating an injury to a body part, comprising the steps of:
   (a) providing an orthopaedic splinting material, including (i) a flexible substrate; and (ii) a moisture-curable resin system impregnated in or coated on said substrate and including a water curable isocyanate functionalized prepolymer, a first catalyst chemically bound-in to said prepolymer, and a second catalyst soluble in water and insoluble in the prepolymer, wherein said second catalyst includes a hydrophilic coating;

(b) exposing the substrate to moisture in an amount sufficient to activate the moisture-curable resin on the substrate; and (c) positioning said splinting material around the body part to be treated and maintaining the splinting material in a preselected position relative to the body part for a sufficient period of time for the splinting material to harden, whereby the splinting material hardens into a rigid supporting structure custom-fitted to the body part to be treated.

3. A resin system, comprising a water curable, isocyanate functionalized prepolymer wherein the curing reaction is catalysed by a first chemically bound-in catalyst arid a second not chemically bound-in catalyst:

(a) said first catalyst comprising a tertiary amine catalyst selected from the group consisting of 1-(2-hydroxyethyl)pyrrolidine, 1-methyl piperazine, 1-methyl-2-piperidine methanol, 1,4-bis(2-hydroxyethyl)piperazine 2[2-(dimethylamino)ethyl] methyl amino ethanol, gramine, 3-morpholino-1,2-propanediol, 1,4-bis(3-aminopropyl)piperazine, tropine, 3-aminopropyl morpholine, 4,2-hydroxyethyl morpholine, 3,3-diamino-N-methyl dipropylamine, 4-bis(2-hydroxypropyl)-2-methylpiperazine 1-(2-hydroxypropyl)imidazole, 3-dimethyl amino propanol, and β-hydroxy-4-morpholine propane sulphonic acid;

(b) said second catalyst is soluble in water and insoluble in said prepolymer; and (c) the first and second catalysts together show a synergistic effect whereby the reaction rate between water and the prepolymer is increased.

4. A resin system comprising at least a water curable, isocyanate functionalized prepolymer, wherein the curing reaction is catalysed by a first chemically bound-in catalyst find a second not chemically bound-in catalyst being coated with a hydrophilic coating.

* * * * *

UNITED STATES PATENT AND TRADEMARK OFFICE
CERTIFICATE OF CORRECTION

PATENT NO. : 6,756,467 B2  Page 1 of 1
APPLICATION NO. : 10/092187
DATED : June 29, 2004
INVENTOR(S) : Michael Francis Shelvey It is certified that error appears in the above-identified patent and that said Letters Patent is hereby corrected as shown below:

Column 9, line 21, delete "catalyst arid a" and enter --catalyst and a--.

Column 10, line 8, delete "4-bis(2-hydroxypropyl)" and enter --1,4-bis(2-hydroxypropyl)".

Column 10, line 19, delete "find a second" and enter --and a second--.

Signed and Sealed this

Twelfth Day of December, 2006

JON W. DUDAS
*Director of the United States Patent and Trademark Office*